(12) United States Patent
Kesner

(10) Patent No.: US 10,863,950 B2
(45) Date of Patent: *Dec. 15, 2020

(54) METHODS AND SYSTEMS FOR RETROSPECTIVE INTERNAL GATING

(71) Applicant: Memorial Sloan Kettering Cancer Center, New York, NY (US)

(72) Inventor: Adam L. Kesner, Los Angeles, CA (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/395,201

(22) Filed: Apr. 25, 2019

(65) Prior Publication Data

US 2019/0350540 A1 Nov. 21, 2019

Related U.S. Application Data

(63) Continuation of application No. 16/178,332, filed on Nov. 1, 2018, now Pat. No. 10,448,903, which is a continuation of application No. 15/728,373, filed on Oct. 9, 2017, now Pat. No. 10,117,625, which is a continuation of application No. 12/151,121, filed on May 5, 2008, now Pat. No. 9,814,431.

(60) Provisional application No. 60/916,200, filed on May 4, 2007.

(51) Int. Cl.
*A61B 6/03* (2006.01)
*A61B 6/00* (2006.01)
*A61B 5/00* (2006.01)

(52) U.S. Cl.
CPC ............. *A61B 6/032* (2013.01); *A61B 6/037* (2013.01); *A61B 6/527* (2013.01); *A61B 5/7289* (2013.01)

(58) Field of Classification Search
None
See application file for complete search history.

(56) References Cited

U.S. PATENT DOCUMENTS

| | | | |
|---|---|---|---|
| 6,144,874 A | 11/2000 | Du | |
| 6,298,260 B1 | 10/2001 | Sontag et al. | |
| 6,501,981 B1 | 12/2002 | Schweikard et al. | |
| 6,539,074 B1 | 3/2003 | Yavuz et al. | |
| 6,556,695 B1 | 4/2003 | Packer et al. | |
| 7,359,535 B2 | 4/2008 | Salla et al. | |
| 7,574,249 B2 | 8/2009 | Piacsek et al. | |
| 7,734,078 B2 | 6/2010 | Prince et al. | |
| 7,756,307 B2 | 7/2010 | Thielemans | |
| 8,229,187 B2 * | 7/2012 | Deller | A61B 5/113 382/128 |
| 9,814,431 B2 * | 11/2017 | Kesner | A61B 6/037 |
| 10,117,625 B2 * | 11/2018 | Kesner | A61B 6/527 |

(Continued)

*Primary Examiner* — William B Perkey
(74) *Attorney, Agent, or Firm* — Foley & Lardner LLP

(57) ABSTRACT

The present invention, in one form, is a method for deriving respiratory gated PET image reconstruction from raw PET data. In reconstructing the respiratory gated images in accordance with the present invention, respiratory motion information derived from individual voxel signal fluctuations, is used in combination to create usable respiratory phase information. Employing this method allows the respiratory gated PET images to be reconstructed from PET data without the use of external hardware, and in a fully automated manner.

22 Claims, 3 Drawing Sheets

(56) References Cited

U.S. PATENT DOCUMENTS

| | | |
|---|---|---|
| 10,448,903 B2 * | 10/2019 | Kesner .................. A61B 6/032 |
| 2004/0218794 A1 | 11/2004 | Kao et al. |
| 2005/0123183 A1 * | 6/2005 | Schleyer .................. G06T 5/20 |
| | | 382/131 |
| 2007/0081704 A1 | 4/2007 | Pan et al. |
| 2007/0127797 A1 | 6/2007 | Angelos et al. |
| 2007/0237372 A1 | 10/2007 | Chen et al. |
| 2008/0226149 A1 | 9/2008 | Wischmann et al. |
| 2008/0253636 A1 | 10/2008 | Deller |
| 2009/0076369 A1 | 3/2009 | Mistretta |
| 2009/0290774 A1 | 11/2009 | Shechter et al. |
| 2009/0299184 A1 | 12/2009 | Walker et al. |
| 2010/0183206 A1 | 7/2010 | Carlsen et al. |

* cited by examiner

METHODS AND SYSTEMS FOR RETROSPECTIVE INTERNAL GATING

CROSS-REFERENCE TO RELATED APPLICATIONS

The present application is a continuation of U.S. patent application Ser. No. 16/178,332, filed Nov. 1, 2018, which is a continuation of U.S. patent application Ser. No. 15/728,373, filed Oct. 9, 2017, which is a continuation of U.S. patent application Ser. No. 12/151,121, filed May 5, 2008, which claims priority to U.S. Provisional Patent Application 60/916,200, filed Jun. 4, 2007, the entire contents of each of which are incorporated herein by reference.

BACKGROUND OF THE INVENTION

This invention relates generally to imaging systems and methods and more particularly to systems and methods for retrospective internal gating.

A large source of image degradation in medical imaging can be attributed to patient motion during the image acquisition, which causes loss of detail in the resultant images. For example respiratory motion causes blurring of the torso. This blurring can be difficult to characterize, and effectively can limit detectability of details, such as small lesions or lesions with low contrasts, and might reduce the accuracy of the measurements for the lesions which are visible.

Respiratory gating in is an approach to lessen the image degradation from respiratory motion by separating the breathing cycle into different phases and generating images from data corresponding to each of these phases. In the past few years there has been much research in developing this approach to imaging, with the hope that this can increase the quality diagnostic information derived from the images. The consensus in literature is that the respiratory gating of images presents a feasible solution to the image degradation introduced by respiratory motion. Researchers have studied the use of respiratory gated PET with respect to improving image quantification, lesion detectability and artifacts, image-coregistration accuracy, and the use of gated PET/CT in radiotherapy treatment planning. A variety of methods has been presented in the above literature for characterizing patient respiratory motion including techniques utilizing cameras, pressure belts, thermometers, point sources, pneumatic sensor systems, and mechanical ventilation (in dogs).

In addition to the above work, which used hardware derived respiratory signals, several software based methods have been proposed which utilize characterization of structural movement to gate the scans.

Acquiring and using software derived respiratory signals have several advantages over hardware based methods. The algorithms are image based, and thus machine independent, and can be used with existing scans, or scanners. What's more, if the algorithm is fully automated then the gated images can be generated without any extra effort or deviation from routine clinical procedures. They come at no additional "cost", other than processing time, and can be generated along side traditional non-gated images.

Another advantage of using image based methods is that they provide assurance of the temporal alignment of the respiratory trace and the image data.

BRIEF DESCRIPTION OF THE INVENTION

In one aspect, a method for retrospective internal gating is described. The method includes acquiring images at different times t1 . . . tn, and identifying temporally cyclical signals, which are combined to create a time varying object motion function which correlates times t1 . . . tn and the phases of the periodic motion.

In another aspect, a computer-readable medium encoded with a program is described. The program is configured to acquire images at different times t1 . . . tn, and identify temporally cyclical signals, which are combined to create a time varying object motion function which correlates times t1 . . . tn and the phases of the periodic motion.

In yet another aspect, a computer is described. The computer is configured to acquire images at different times t1 . . . tn, and identify temporally cyclical signals, which are combined to create a time varying object motion function which correlates times t1 . . . tn and the phases of the periodic motion.

DETAILED DESCRIPTION OF THE INVENTION

Figure 1:
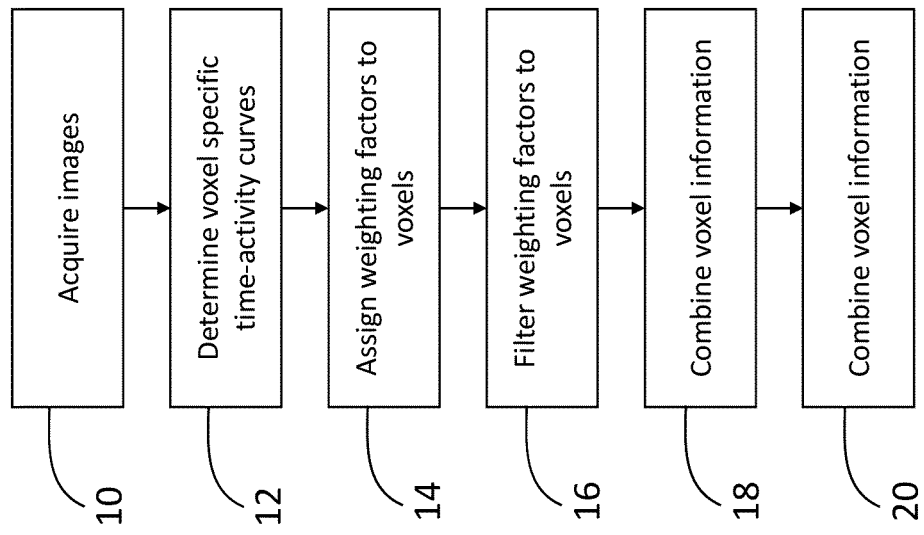
FIG. 1: A flowchart of an embodiment of a method for retrospective internal gating

Contemporary medical imaging produces 2D or 3D representations of patient anatomy or biological function. Several common type of medical imaging devices are Computed Tomography, Positron Emission tomography, Magnetic resonance imaging.

In Computed Tomography (CT), an x-ray source and a detector are rotated around a patient, within the imaging plane, and projections measured by the detector are gathered at various angles. These projections can then used in a reconstruction algorithm, to generate images spatially mapping attenuation characteristics of the patient.

In Positron Emmision Tomography (PET), a patient is administered a radiopharmaceutical, and placed within the field of view of a fixed ring of detectors. The detectors measure the gamma rays resulting from positron annihilation happening at the location of isotope. A reconstruction algorithm can then be applied to generate an image of the estimated spatial distribution of the radiopharmaceutical within the patient.

In Magnetic Resonance Imaging, the magnetic moment of nuclei are placed within an oscillating magnetic field, and different characteristics of there behavior are used to generate information, allowing for the creation of a anatomical or functional map. To achieve these images, information is spatially localized through the application of variations in the applied magnetic field. These variations can be applied in the form of gradients leaving only a slice of anatomy on-resonance to contribute to the signal.

Regardless of the imaging technique employed, all methods suffer from artifacts relating to patient motion. Sources of motion include respiration, and cardiac rhythms. Efforts have been made to create images corrected for this motion.

As used herein, an element or step recited in the singular and preceded with the word "a" or "an" should be understood as not excluding plural the elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Additionally, although the herein described methods are described in a medical setting, it is contemplated that the benefits of the methods accrue to non-medical imaging systems such as those systems typically employed in an industrial setting or a transportation setting, such as, for example, but not limited to, a baggage scanning system for an airport, other transportation centers, government buildings, office buildings, and the like. The benefits also accrue to micro PET and CT systems which are sized to study lab animals as opposed to humans.

FIG. 1 illustrates an embodiment of a method for retrospective internal gating. The method includes acquiring 10 digital images i1 . . . in at times t1 . . . tn to obtain a chronologically ordered image set, where temporal sampling is short relative to periodic motion being studied, and no greater than one half the expected period. Images may be realized using any form of imaging system. As an example, images i1 . . . in are 3D PET images acquired at periods corresponding to 0.5 second time windows, which is a plausible bin time to account for signal from human respiration. Examples of motion information include respiratory motion information and cardiac motion information.

Figure 2:
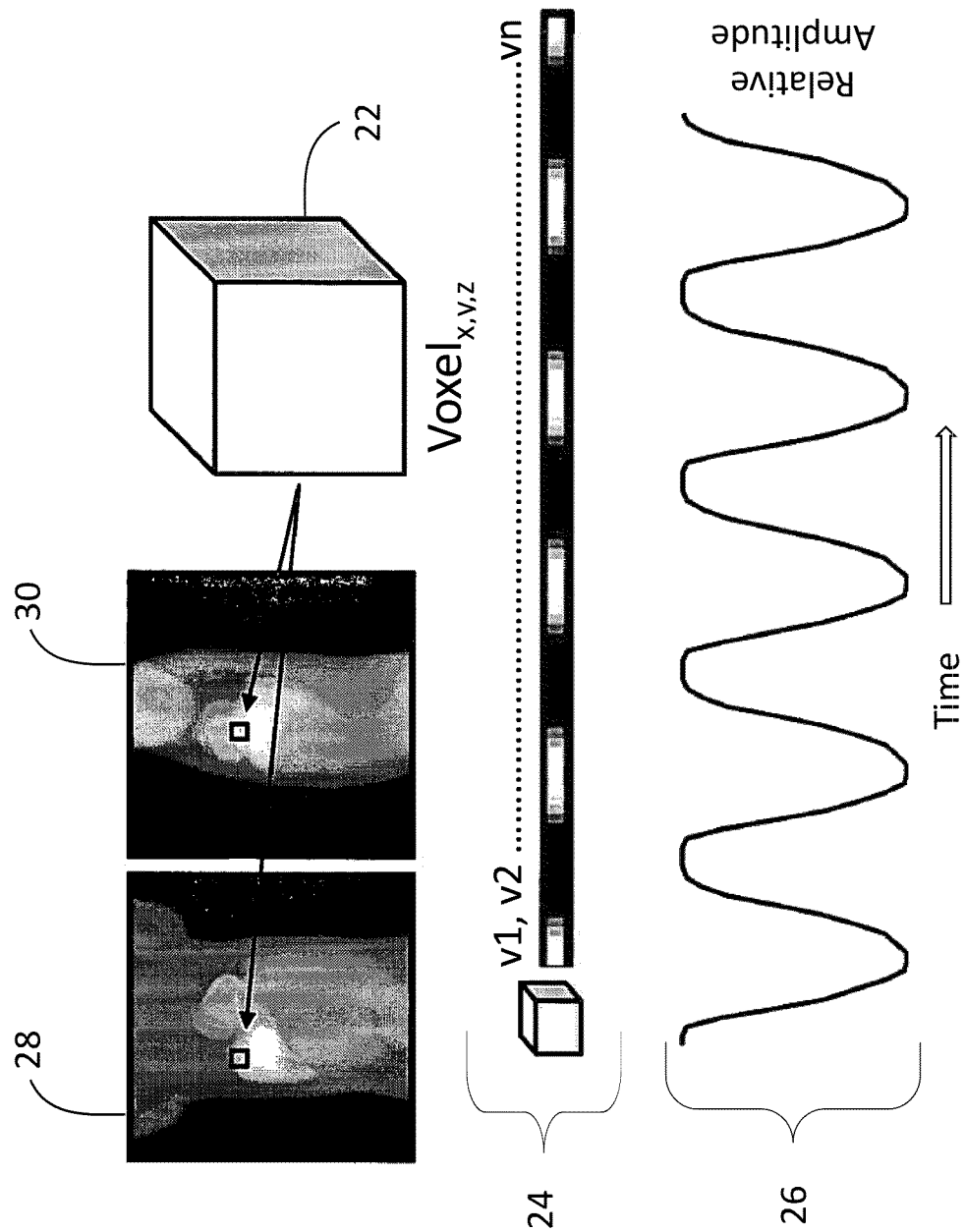
FIG. 2: Simulated time-activity curve for single voxel (noiseless simulation). (Top left) Image volume projections, (Top right) illustration of sample voxel, (bottom) time-activity curve of voxel. Projection 28 corresponds with a coronal projection (noiseless), and projection 30 corresponds with a sagittal projection (noiseless).

FIG. 2 offers visualization of time-activity 12 information specific for a sample individual voxel. This time-activity 26 is derived by organizing into a single discrete array the values v1 . . . vn 24 of an individual voxel 22 in the successive images i1 . . . in. The individual voxel locations in each individual image represent a volumes of space at time ti. The voxel values represent the signal of interest in the image, i.e. for PET the value would represent radioactivity concentration.

Voxel weighting factors 14 can be assigned to individual voxels establishing their importance during processing 18. In one embodiment, the weighting factor can be based upon the mean value of that voxel's 22 time-activity 26 information, values v1 . . . vn 24. In another embodiment that weighting factor can be based upon proximity to spatial activity gradients apparent in the images being used. A weighting factor of 0 can also be applied to voxels that the algorithm need not spend time processing. Weighting factors can be applied to some, none, or all voxels.

Voxel time-activity 26 information contained in v1 . . . vn 24 may have unwanted frequencies filtered out using frequency filters. For example, when methods are being used for respiratory gating, non respiratory frequencies (less than 2 seconds and greater than 15 seconds) can be filtered out or attenuated in the time-activity signals. This can be done to reduce the effects of noise in the signal. Other possible filters can be envisioned, such as ramp filters and Gaussian filters.

Information is combined from many voxels' time-activity 26 values to create a time varying object motion function. This is achieved by evaluating voxels and their respective time-activity information individually.

In one embodiment, voxels can be prioritized for processing by their weighting factors 14 defined earlier. The time varying object motion function is a summation of filtered individual voxel time-activity 26 curves.

Figure 3:
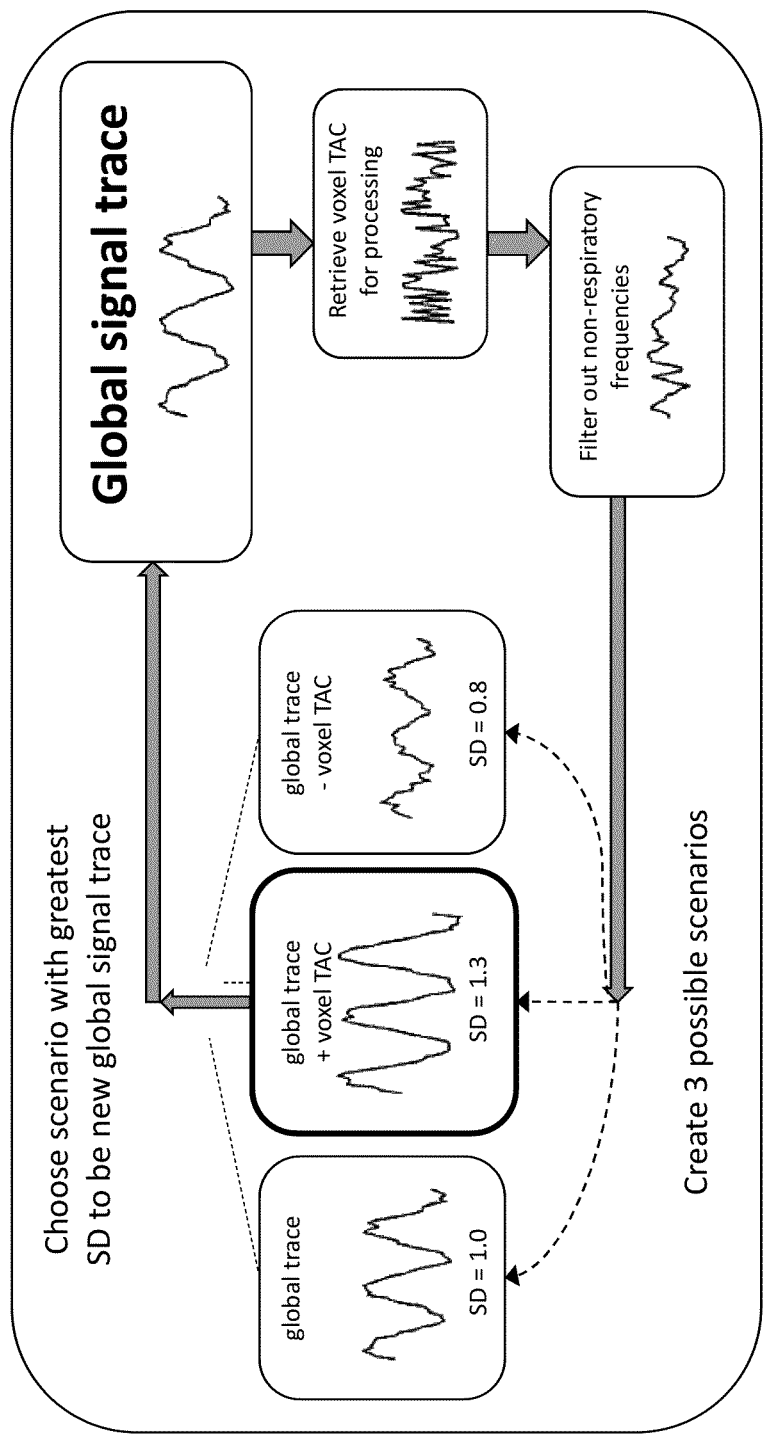
FIG. 3: Flow chart summarizing main steps in image processing loop, illustrated for one possible embodiment with example curves. With each new voxel processed, the time varying object motion function is updated. (SD=standard deviation).

In one embodiment, the processing is initiated by defining the time varying object motion function as the filtered time-activity values 30 of the voxel with the highest priority determined by the weighting factors 14. Subsequent filtered voxel time-activity values are synthesized, in order of priority, into a time varying object motion function using the following steps, shown in FIG. 3:

1) The filtered time-activity values of the voxel are combined with the current time varying object motion function in three possible scenarios 36:
   (A) time varying object motion function (unchanged)
   (B) time varying object motion function+voxel time-activity values
   (C) time varying object motion function−voxel time-activity values 2) Of the three, the scenario with the highest standard deviation is chosen to serve as the new time varying object motion function 38 (i.e. the function with the greatest difference between peaks and valleys).

3) Unless the stopping criteria are met 34, the process is repeated for the next voxel.

With each iteration, and for each new voxel processed, the time varying object motion function 32 either remains the same, or is improved. In one embodiment these iterations may be set a priori to stop after the first 500 voxels are processed. Or, in another embodiment, they may be slated to stop after processing the voxel with a weighting factor above a specified threshold. In yet another embodiment, every voxel within the image space may be processed. In still yet another embodiment, voxels may be processed until the time varying object motion function meets a set criterion.

The purpose of step (1) is to determine the best contribution an individual voxel can make to the time varying object motion function. The scenarios using addition and subtraction are included to account for the fact that voxels may be in or out of phase with the time varying object motion function, depending on whether they were positioned superior or inferior to gradients of motion. Other embodiments using different methods of evaluating step (1) above can be envisioned.

Once the chosen stopping criteria are met, the current time varying object motion function 40 is returned for use in the mapping of image data to phase of motion.

Final phase information 20 for the motion of the imaged object can be extracted from the timing of the peaks and dips in the time varying object motion function. In one embodiment, relating to respiratory motion, local maxima and local minima on the time varying object motion function may be characterized as corresponding to the timing of full inspiration and full expiration, respectively.

While the invention has been described in terms of various specific embodiments, those skilled in the art will recognize that the invention can be practiced with modification within the spirit and scope of the claims.

What is claimed is:

1. A method for retrospective internal gating comprising:
   acquiring image data corresponding to times t1 . . . tn to be used to generate one or more images corresponding to a moving object;

extracting information for a plurality of arrays derived from the image data;
generating a time varying object motion function based on the extracted information for the plurality of arrays of the image data;
determining, using the time varying object motion function, phase information for motion of the moving object; and
generating at least one image correcting for the motion of the moving object using the determined phase information for motion of the moving object and the acquired image data.

2. The method of claim 1, wherein information is defined as a signal of an array element over times t1 . . . tn.

3. The method of claim 1, further comprising assigning weighting factors to the plurality of arrays, wherein the weighting factors include array specific weighting factors based on the mean array activity over times t1 . . . tn.

4. The method of claim 1, further comprising assigning weighting factors to the plurality of arrays, wherein the weighting factors include array specific weighting factors based upon the array's proximity to greater spatial signal gradients on a non-corrected image.

5. The method of claim 4, wherein the non-corrected image is comprised of combined image data from times t1 . . . tn.

6. The method of claim 1, further comprising assigning weighting factors to the plurality of arrays, wherein the weighting factors include array specific weighting factors assigned based on magnitude of signal variation over times t1 . . . tn, for each array.

7. The method of claim 1, wherein at least some arrays of the plurality of arrays are deemed unimportant and weighted at zero usage value.

8. The method of claim 1, wherein information is filtered in frequency space for windows encompassing expected valid periodicity of the motion.

9. The method of claim 8, wherein the frequency window used may be adjusted to be patient or data specific.

10. The method of claim 8, wherein the frequency window may be adjusted over times t1 . . . tn.

11. The method of claim 1, wherein array information is processed serially in order of prioritization to yield a time varying object motion function.

12. The method of claim 11, wherein the time varying object motion function spans t1 . . . tn.

13. The method of claim 1, wherein the initial time varying object motion function is assigned to be the curve of the array with the highest priority.

14. The method of claim 1, wherein individual array information is combined with the evolving time varying object motion function in three possible scenarios: the first scenario is leaving the current time varying object motion function unaltered, the second scenario is adding the individual array information to the current time varying object motion function, and the third scenario is subtracting the individual array information from the current time varying object motion function, to account for possible phase mismatch; of these three scenarios, the one with the most significant improvement is chosen as the new time varying object motion function, to be used in evaluation of the next voxel.

15. The method of claim 1, further comprising assigning weighting factors to the plurality of arrays.

16. The method of claim 1, wherein determining, using the time varying object motion function, the phase information for motion of the moving object is based upon identifying non-recurring patterns in the time varying object motion function.

17. The method of claim 1, wherein the determining, using the time varying object motion function, the phase information for motion of the moving object is based upon identifying recurring patterns in the time varying object motion function.

18. The method of claim 1, further comprising mapping of image data to corresponding motion phases using the time varying object motion function, wherein mapped image data is reordered and categorized in such a way that images within a category all appear to be taken at the same phase of motion.

19. The method of claim 1, wherein the acquired data includes data for a respiratory cycle of a subject corresponding to the moving object.

20. The method of claim 1, wherein acquiring the image data includes acquiring the image data for a greater amount of time than one breath cycle of a subject corresponding to the moving object.

21. A non-transitory computer-readable medium encoded with a program that when executed by one or more processors cause a machine to:
acquire image data corresponding to times t1 . . . tn to be used to generate one or more images corresponding to a moving object;
extract information for a plurality of arrays derived from the image data;
generate a time varying object motion function based on the extracted information for the plurality of arrays of the image data;
determine, using the time varying object motion function, phase information for motion of the moving object; and
generate at least one image correcting for the motion of the moving object using the determined phase information for motion of the moving object and the acquired image data.

22. A system comprising:
one or more processors; and
a non-transitory computer-readable medium having instructions stored thereon that when executed by the one or more processors cause the system to:
acquire image data corresponding to times t1 . . . tn to be used to generate one or more images corresponding to a moving object;
extract information for a plurality of arrays derived from the image data;
generate a time varying object motion function based on the extracted information for the plurality of arrays of the image data;
determine, using the time varying object motion function, phase information for motion of the moving object; and
generate at least one image correcting for the motion of the moving object using the determined phase information for motion of the moving object and the acquired image data.

* * * * *